United States Patent
Suh et al.

(10) Patent No.: US 9,693,811 B2
(45) Date of Patent: Jul. 4, 2017

(54) CERVICAL SPINE SPACER

(71) Applicant: GLOBUS MEDICAL, INC., Audubon, PA (US)

(72) Inventors: Sean Suh, Jamesburg, NJ (US); Jon Suh, Blue Bell, PA (US); Ryan Watt, Boyertown, PA (US)

(73) Assignee: GLOBUS MEDICAL, INC, Audubon, PA (US)

( * ) Notice: Subject to any disclaimer, the term of this patent is extended or adjusted under 35 U.S.C. 154(b) by 18 days.

(21) Appl. No.: 14/559,944

(22) Filed: Dec. 4, 2014

(65) Prior Publication Data

US 2015/0112386 A1 Apr. 23, 2015

Related U.S. Application Data

(63) Continuation of application No. 13/303,786, filed on Nov. 23, 2011, now Pat. No. 8,926,666.

(51) Int. Cl.
*A61B 17/70* (2006.01)
*A61F 2/44* (2006.01)
*A61F 2/30* (2006.01)

(52) U.S. Cl.
CPC .......... *A61B 17/7064* (2013.01); *A61B 17/70* (2013.01); *A61F 2/442* (2013.01); *A61F 2/4455* (2013.01); *A61F 2/4465* (2013.01); *A61F 2002/3082* (2013.01); *A61F 2002/30131* (2013.01); *A61F 2002/30785* (2013.01); *A61F 2002/30828* (2013.01); *A61F 2002/30843* (2013.01); *A61F 2002/4475* (2013.01); *A61F 2310/00023* (2013.01)

(58) Field of Classification Search
CPC .......... A61B 17/70; A61F 2/442; A61F 2/4465
USPC .............................. 623/17.11–17.16; 606/249
See application file for complete search history.

(56) References Cited

U.S. PATENT DOCUMENTS

| | | | |
|---|---|---|---|
| 4,904,261 A | 2/1990 | Dove | |
| 5,558,674 A | 9/1996 | Heggeness | |
| 5,961,554 A | 10/1999 | Janson | |
| 6,485,518 B1 | 11/2002 | Cornwall et al. | |
| 6,613,089 B1 | 9/2003 | Estes et al. | |
| 6,974,480 B2* | 12/2005 | Messerli | A61B 17/1671 623/17.11 |
| 7,303,583 B1* | 12/2007 | Schar | A61F 2/442 623/17.16 |
| 2004/0093083 A1* | 5/2004 | Branch | A61B 17/1671 623/17.11 |
| 2004/0210219 A1 | 10/2004 | Bray | |
| 2004/0225360 A1 | 11/2004 | Malone | |
| 2005/0119747 A1* | 6/2005 | Fabris Monterumici | A61B 17/025 623/17.11 |

(Continued)

*Primary Examiner* — Christopher Beccia

(57) ABSTRACT

A cervical spine spacer includes a spacer body configured to be disposed between adjacent cervical vertebrae in the cervical spine and to maintain a desired spacing between the adjacent cervical vertebrae. The cervical spine spacer also includes a channel passing completely through the spacer body from a first surface of the spacer body to a second surface of the spacer body and a fastener configured to pass through the channel. At least one of the first surface and the second surface is configured to contact one of the adjacent cervical vertebrae and the channel is sized to accommodate the fastener passing through the channel at a plurality of angles.

19 Claims, 11 Drawing Sheets

(56) References Cited

U.S. PATENT DOCUMENTS

| | | | |
|---|---|---|---|
| 2005/0256578 A1* | 11/2005 | Blatt | A61B 17/1757 623/17.15 |
| 2008/0015701 A1* | 1/2008 | Garcia | A61B 17/1671 623/17.16 |
| 2008/0183293 A1* | 7/2008 | Parry | A61F 2/447 623/17.11 |
| 2008/0249575 A1* | 10/2008 | Waugh | A61F 2/447 606/305 |
| 2009/0163957 A1 | 6/2009 | St. Clair et al. | |
| 2010/0305704 A1* | 12/2010 | Messerli | A61F 2/442 623/17.16 |
| 2011/0040382 A1 | 2/2011 | Muhanna | |

* cited by examiner

CERVICAL SPINE SPACER

CROSS REFERENCE TO RELATED APPLICATION

This application is a continuation of U.S. patent application Ser. No. 13/303,786 filed Nov. 23, 2011, the contents of which are incorporated herein by reference in its entirety for all purposes.

FIELD OF THE INVENTION

The present invention relates to cervical spine stabilization and spacing devices.

BACKGROUND OF THE INVENTION

The top seven vertebrae in the spine, vertebrae C1 through C7, form the cervical spine. Adjacent vertebrae in the cervical spine interface at two sets of opposing articulated surfaces each with an intervertebral disc. Trauma to the cervical spine, degenerative conditions such as arthritis and genetic disorders can cause fractures in the vertebrae, damage to intervertebral discs, pressure on the spinal cord or other nerves and misalignment or improper spacing between adjacent vertebrae. The result is pain, discomfort and other symptoms including periods of confusion or conscious awareness that does not seem normal, difficulty swallowing or saying words due to loss of muscle control after damage to the nervous system (dysarthria), dizziness, loss of sensation, pain in the back of the head, loss of the ability to know how joints are positioned, tingling or numbness in the hands or fingers, tingling or numbness in the arms, tingling when the neck bends forward or backward and weakness or stiff and awkward movements of the of the arms and legs.

One such condition is basilar invagination, which occurs when the top of the C2 vertebra, e.g., the axis, migrates upward toward the C1 vertebra, e.g., the atlas. As the base of the skull rests on the C1 vertebra and the odontoid process extends from the axis up though the atlas, this upwards migration can cause the opening in the skull where the spinal cord passes through to the brain to narrow and may also press on the lower brainstem. Treatment for basilar invagination and other symptoms associated with other conditions in the cervical spine includes both surgical and non-surgical techniques.

While some patients respond well to non-surgical treatments, others require surgery. These surgical techniques include replacing discs and repairing vertebrae using bone grafts. A cervical plate is screwed into the superior and inferior vertebral bones, which stabilizes the cervical spine facilitating fusion and healing. In addition, screws are used to mend fractured vertebrae including a fractured odontoid process. Maintaining proper alignment and spacing between adjacent vertebral bones is important. The use of a screw passing between the adjacent articular facets does not guarantee that the proper spacing is maintained. In addition, re-establishing and maintaining proper spacing between the axis and the atlas can prevent or alleviate basilar invagination.

SUMMARY OF THE INVENTION

Exemplary embodiments of the present invention are directed to cervical spine spacers that maintain or re-establish proper spacing between adjacent vertebrae in the cervical spine. These cervical spine spacers can be used in combination with bone grafts, stabilizing the cervical spine and acting as a cover or sheath for the bone graft. In addition, these cervical spine spacers accommodate the geometries found between adjacent articular facets all along the cervical spine and allow passage of a screw through the spacer at a variety of angles. In one embodiment, these cervical spine spacers can be used between the bodies of the cervical vertebrae at locations other than between opposing articular facets.

The present invention is directed to a cervical spine spacer having a spacer body configured to be disposed between adjacent cervical vertebrae in the cervical spine and to maintain a desired spacing between the adjacent cervical vertebrae and a channel passing completely through the spacer body from a first surface of the spacer body to a second surface of the spacer body. At least one of the first surface and the second surface of the spacer body is configured to contact one of the adjacent cervical vertebrae. The cervical spine spacer also includes a fastener extending completely through the channel and configured to anchor the spacer body between the adjacent cervical vertebrae. The channel is configured to accommodate a fastener extending through the channel and intersecting each one of the first surface and the second surface at a plurality of different angles.

In one embodiment, the first surface is configured to contact a first cervical vertebra, and the second surface is configured to contact a second cervical vertebra. Suitable first cervical vertebra include the C1, C2, C3, C4, C5 and C6 vertebra, and suitable second cervical vertebra include the C2, C3, C4, C5, C6 and C7 vertebra. In one embodiment, the first surface is configured to contact an inferior articular facet of the first cervical vertebra, and the second surface is configured to contact a superior articular facet of the second cervical vertebra. For example, the first cervical vertebra is the C1 vertebra and the second cervical vertebra is the C2 vertebra.

In one embodiment, the first surface includes a plurality of pointed protrusions extending out from the first surface and configured to contact the first cervical vertebra, and the second surface also includes a plurality of pointed protrusions extending out from the second surface and configured to contact the second cervical vertebra. In one embodiment, the channel includes a first opening in the first surface and a second opening in the second surface. The first opening extends from a front face of the spacer body partially across the first surface towards a back face of the spacer body, and the second opening is disposed in the second surface and extends from the back face partially across the second surface. The back face is opposite the front face, and the back face and the front face extend between the first surface and the second surface. In one embodiment, the first opening extends partially along the front face from the first surface toward the second surface, and the second opening extends partially along the back face from the second surface toward the first surface.

In one embodiment, the front face has a first height between the first surface and the second surface, and the back face has a second height between the first surface and the second surface. The first height is less than the second height.

In one embodiment, the spacer body has a spacer portion configured to be disposed between the adjacent cervical vertebrae and an anchor plate portion extending from the spacer portion, the channel passing through the anchor plate portion. The anchor plate portion extends from the spacer portion at an angle of about 90°. The adjacent cervical vertebrae are the C1 vertebra and the C2 vertebra, and the first surface of the spacer body is located on the anchor plate portion and is configured to contact an anterior surface of the C2 vertebra. The channel passes through the anchor plate portion intersecting the first surface and the second surface at an angle configured to direct a fastener through the anterior surface of the C2 vertebra from an inferior position toward an odontoid process of the C2 vertebra.

In one embodiment, the spacer body comprises two spacer portions. The anchor plate portion is U-shaped having two arms, and each spacer portion extends from a given arm of the U-shaped anchor plate portion at the 90° angle. The spacer portion is configured to be disposed between an anterior arch of the C1 vertebra and the body of the C2 vertebra between one of a pair of superior articular facets and the odontoid process. When the spacer body includes two spacer portions, each spacer portion extends from the anchor plate and is disposed between the anterior arch of the C1 vertebra and the body of the C2 vertebra such that each spacer body is on an opposite side of the odontoid process.

DETAILED DESCRIPTION

Figure 1:
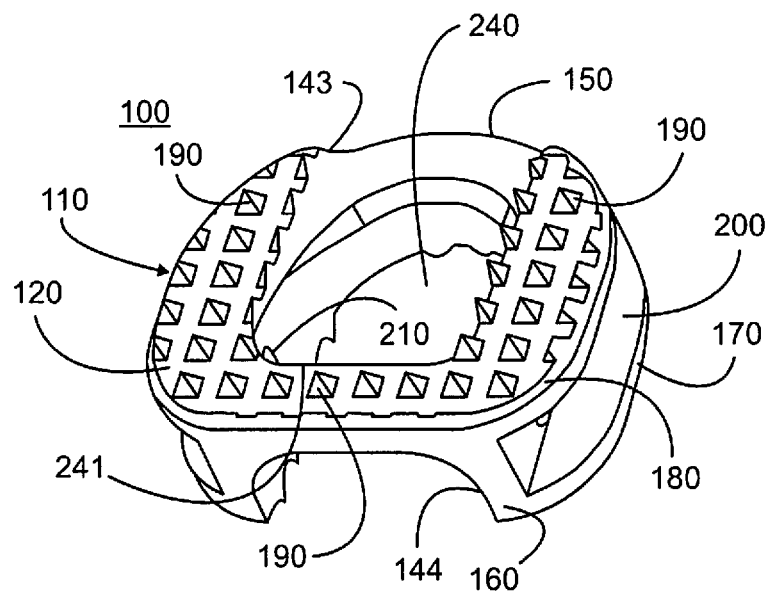
FIG. 1 is a top perspective view of an embodiment of a cervical spine spacer in accordance with the present invention.
Figure 2:
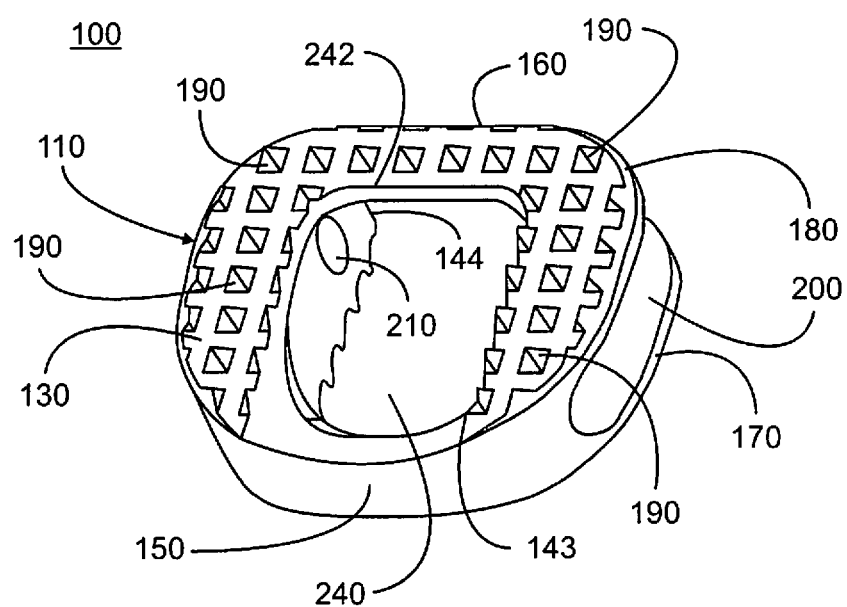
FIG. 2 is a bottom perspective view of the embodiment of FIG. 1.
Figure 3:
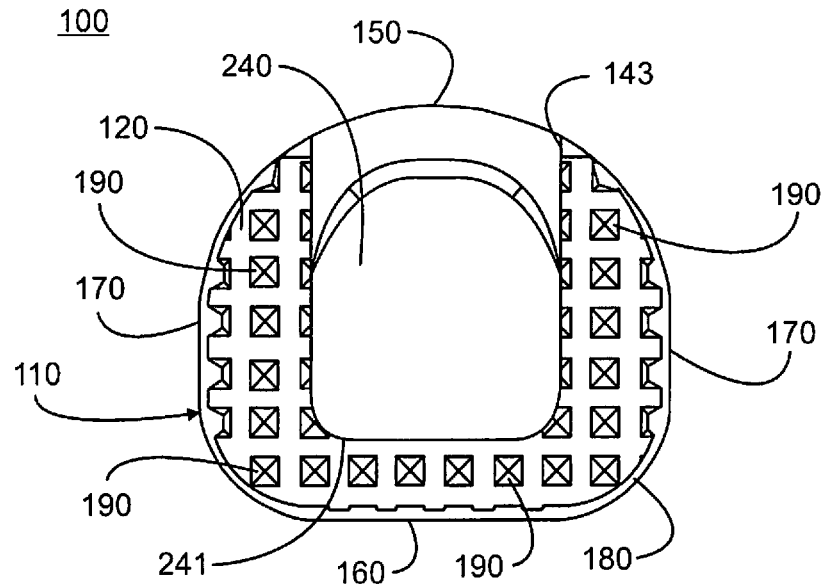
FIG. 3 is a top view of the embodiment of FIG. 1.
Figure 4:
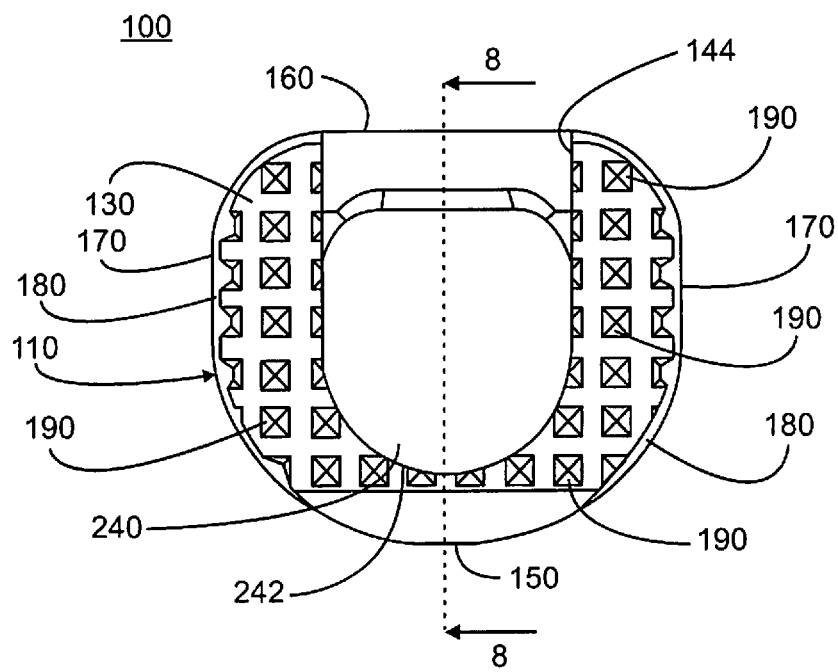
FIG. 4 is bottom view of the embodiment of FIG. 1.
Figure 5:
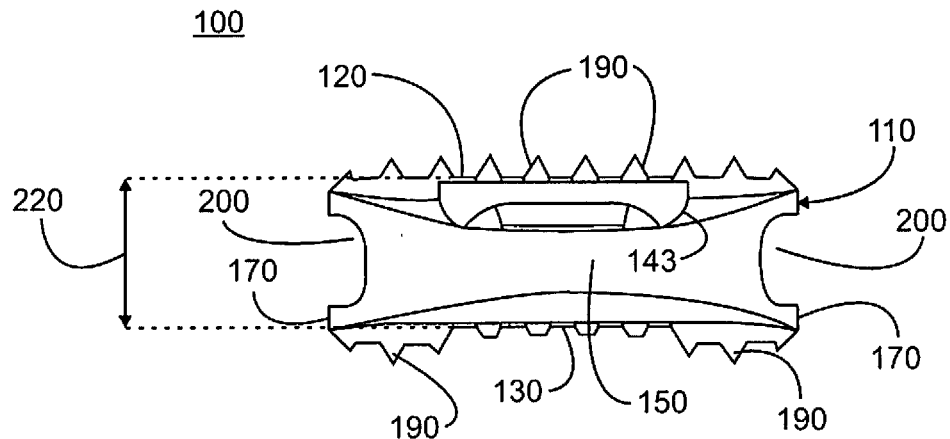
FIG. 5 is a front elevation view of the embodiment of FIG. 1.
Figure 6:
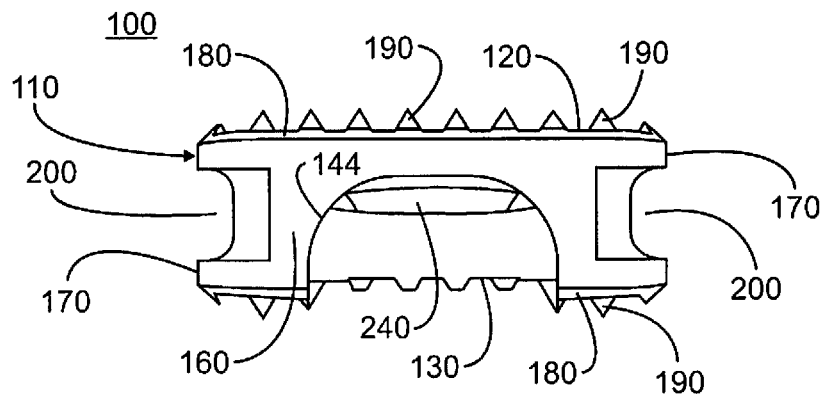
FIG. 6 is a back elevation view of the embodiment of FIG. 1.

Referring initially to FIGS. 1-7, an exemplary embodiment of a cervical spine spacer 100 in accordance with the present invention is illustrated. The cervical spine spacer includes a spacer body 110. The spacer body is configured to be disposed between and to fit between adjacent cervical vertebrae in the cervical spine. These adjacent cervical vertebrae include a first cervical vertebra that can be the C1, C2, C3, C4, C5 or C6 vertebra and a second cervical vertebra that can be the C2, C3, C4, C5, C6 or C7 vertebra. In one embodiment, the first cervical vertebra is the C1 vertebra, and the second cervical vertebra is the C2 vertebra. The spacer body is sized and shaped to maintain or to re-establish a desired spacing between the adjacent cervical vertebrae. Therefore, the spacer body is constructed from a material that is suitable to be inserted into the cervical spine and that can withstand the movement and forces between adjacent vertebrae in the cervical spine. Suitable materials include, but are not limited to metals such as metals such as titanium and stainless steel, plastics and polymers such as PEEK and PET, Bionate and elastomers.

The spacer body 110 includes a first surface 120 and a second surface 130 opposite the first surface. When placed between a given pair of adjacent vertebrae in the cervical spine, at least one of the first surface and the second surface is in contact with one of the vertebrae in that given pair of adjacent vertebrae. The first and second surfaces can contact any portion of a given cervical vertebra, including the body, the anterior arch, the posterior arch, the anterior tubercle, the posterior tubercle, the lateral mass and the transverse process. In one embodiment, the adjacent cervical vertebrae are contacted at opposing articular surfaces or articular facets, for example, an inferior articular facet of the first cervical vertebra and an opposing superior articular facet on the second cervical vertebra. In one embodiment, both the first surface and second surface contact one of the vertebrae in the given pair of adjacent cervical vertebrae.

The spacer body 110 also includes a front face 150 and a back face 160 opposite the front face. The front and back faces extend between the first and second or top and bottom surfaces of the spacer body. In one embodiment, the back and front faces extend generally perpendicular to the first and second surfaces, although the front and back faces can intersect the first and second surfaces at angles other than 90 degrees. In one embodiment, the front and back faces are configured to be aligned with the anterior and posterior sides of the cervical spine when the cervical spacer is placed between adjacent cervical spine vertebrae. The spacer body also includes a pair of opposing side faces 170 that also extend from the first surface to the second surface. Each side face runs from the front face to the back face. In one embodiment, the side faces extend generally perpendicular to the first and second surfaces, although the side faces can intersect the first and second surfaces at angles other than 90 degrees. In one embodiment, the transitions between the first and second surfaces and the front face, the back face and the side faces include a beveled edge 180. The spacer body thus includes a beveled edge that rounds around at least a portion of the perimeter of the first surface and the second surface. This beveled edge advantageously minimizes or eliminates sharp edges that could hinder insertion of the spacer body or that could scrape the vertebrae. In one embodiment, the side faces are configured to be aligned with the lateral sides of the cervical spine when the cervical spacer is placed between adjacent cervical spine vertebrae.

The spacer body is generally rectangular or square in shape; however, the transitions, e.g., the corners of the rectangular shape, between the front and back faces and the side faces are rounded. In some embodiments, the transitions between the front face and the side faces and the back face and the side faces are not identical. Therefore, the spacer body is not symmetrical front to back; however, the spacer body is preferably symmetrical side to side. In one embodiment, the rounded transitions from the side faces to the front face have a greater radius or are smoother than the rounded transitions from the side faces to the back face. Therefore, the front face of the spacer body has a more rounded appearance, and the back face has a more squared appearance. In general, the shape of the spacer body, including the transitions among the faces, is chosen such that it mirrors or conforms to the shape of the portion of the cervical spine vertebrae that it contacts. For example, the transitions among the faces are configured to fit between opposing articular facets within the space occupied by intervertebral discs. In addition, all of the dimensions of the spacer body are selected to fit within the space between opposing articular facets.

In one embodiment, the spacer body includes a plurality of pointed protrusions 190 located on at least one of the first surface and the second surface. In some embodiments, the pointed protrusions are located on both the first surface and the second surface. In one embodiment, each pointed protrusion is shaped as a pyramid having a square or rectangular base and extends out from the first or second surface. The pyramid shape can be truncated, e.g., frusto-conical, and the pyramid shaped pointed protrusions along the edges of the spacer body can be shaved or clipped by the beveled edge of the spacer body. The pointed protrusions are configured to contact the first cervical vertebra and the second cervical vertebra in the adjacent pair of cervical vertebrae between which the spacer body is positioned. This assists in holding the spacer body in place and prevents undesired movement between the spacer body and the cervical vertebrae.

The spacer body includes a groove 200 running along each side face and extending into the spacer body. The groove has a rectangular or rounded cross section and preferably extends along the entire length of each side face. The groove removes mass from the spacer body and also provides a surface for gripping the spacer body using an insertion tool such that the insertion tool does not extend outside the dimensions of the spacer body. At least one and preferably two holes 210 are provided passing completely through the spacer body. These holes extend through the spacer body perpendicular to the grooves, and the ends of the holes are located in the grooves. These holes also provide a gripping surface for an insertion tool and also provide access to structures such as bone grafts that are surrounded by or contained within the spacer body.

Figure 7:
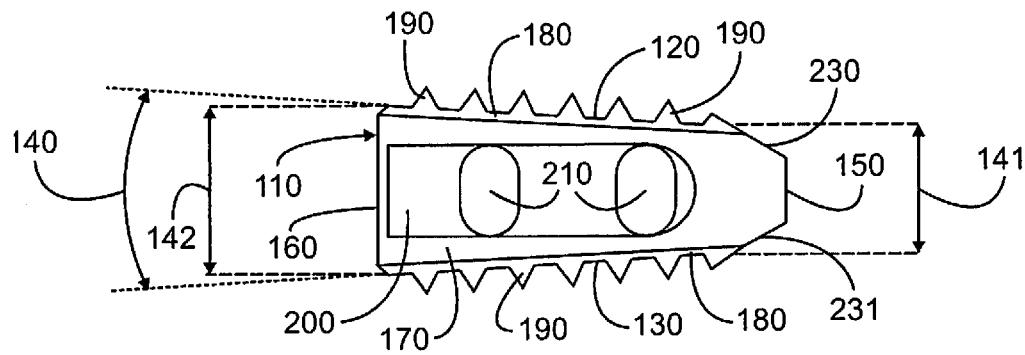
FIG. 7 is a side elevation view of the embodiment of FIG. 1.

The spacer body is configured to have a desired thickness or height 220 (FIG. 5) defined between the first surface and the second surface. This thickness is selected based upon the desired spacing to be maintained or established between the adjacent cervical vertebrae. Therefore, the selected thickness can vary depending on the exact vertebra in the adjacent pair of vertebrae and on the location of the cervical spacer between the adjacent pair of vertebrae, e.g., between opposing articular facets or between opposing transverse processes. In one embodiment, the thickness is constant between the side faces or the spacer body but varies between the front face 150 and the back face 160 (FIG. 7). For example, the thickness is smaller at the front face and larger at the back face. In one embodiment, the front face has a first height 141 between the first surface and the second surface, and the back face has a second height 142 between the first surface and the second surface. The first height is less than the second height. The difference in thickness represents an angle 140 between the first surface and the second surface when moving from the front face to the back face. This angle can be varied and matches, for example, changes in distance between opposing portions of the adjacent vertebrae such as opposing articular facets. In one embodiment, this angle is between about 5° and about 10°, preferably about 7°. The spacer body can also include steeper or larger beveled surfaces 230, 231 adjacent the front face between the first surface and the second surface. This larger beveled surface is larger than the beveled perimeter 180 and facilitates insertion of the spacer body between the adjacent cervical vertebrae.

The cervical spine spacer 100 also includes a channel 240 passing completely through the spacer body 110 from the first surface of the spacer body to the second surface of the spacer body. The channel 240 includes a first opening 241 in the first surface and a second opening 242 in the second surface. In one embodiment, the first opening and second opening are completely contained within the first surface and the second surface and do not extend to the edges of the first and second surfaces. Preferably, the first opening extends from the front face, e.g., the edge where the front face meets the first surface, of the spacer body partially across the first surface towards a back face of the spacer body. Similarly, the second opening extends from the back face, e.g., the edge where the back face meets the second surface, partially across the second surface toward the front face. In some embodiments, the first opening does not extend completely to the back face, and the second opening does not extend completely to the front face. In addition, both the first and second openings do not extend completely to the side faces.

In one embodiment, the first opening includes a front face portion 143 that extends partially along the front face from the first surface toward the second surface, and the second opening includes a back face portion 144 that extends partially along the back face from the second surface toward the first surface. Although the channel extends along the front face and the back face, the channel is completely enclosed by the spacer body.

Figure 8:
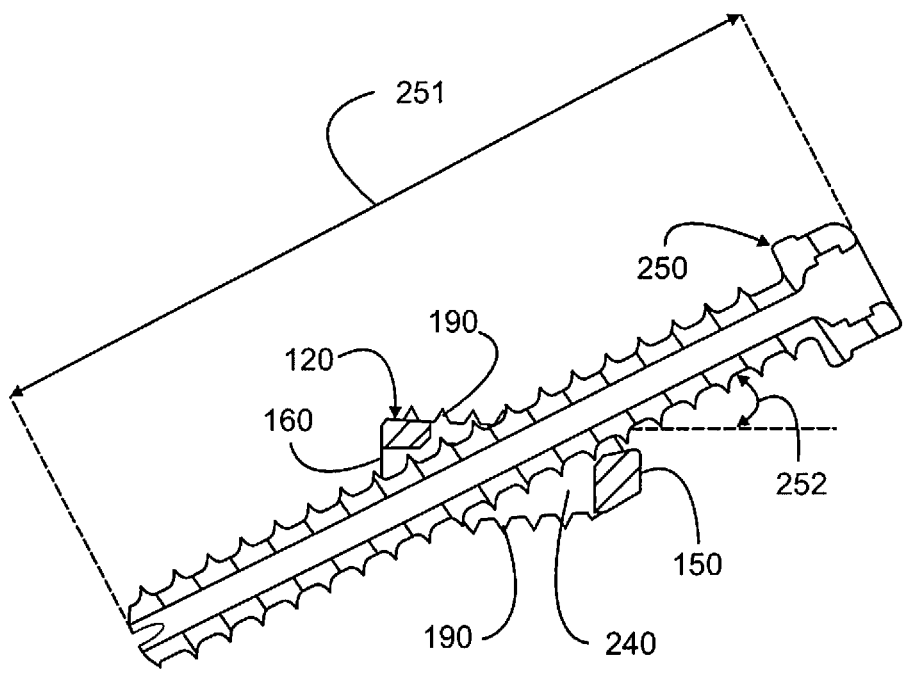
FIG. 8 is cross section view of an embodiment of a cervical spine spacer in accordance with the present invention including a fastener.

Referring to FIG. 8, in one embodiment, the cervical spine spacer includes at least one fastener 250. Suitable fasteners and fastener materials for use with spinal implants are known and available in the art and include screws such as titanium screw. The fastener is configured to pass completely through the channel 240 and into at least one or both of the vertebrae in the adjacent pair of cervical vertebrae. Therefore, the fastener has an overall length sufficient to extend through the spacer body and into the cervical vertebrae. In one embodiment, this length is sufficient to pass through the first vertebra, through the channel and into the second vertebra. In one embodiment, the channel is also configured to be large enough to surround or act as a sheath for a bone graft placed between the adjacent vertebrae. As the geometry of the spine varies depending on the location of the cervical spine spacer, and the fastener may be inserted into the vertebrae and through the channel from a variety or directions, e.g., anterior, posterior, lateral, superior and inferior, the angle 252 between the fastener and at least one of the first surface and the second surface will vary. Therefore, the channel is configured to accommodate a fastener extending through the channel and intersecting each one of the first surface and the second surface at a plurality of different angles. The larger the first and second openings of the channel, the greater the range of angles accommodated. By including the front face portion and the back face portion of the first and second openings, and even greater range of angles is accommodated. In particular, rather small angles are accommodated as would be found in applications where the interface, e.g., the opposing articular facets, forms an angle of less than 45% with the axis of the cervical spine. It also accommodates approaching a cervical spacer from the front face of the back face at a rather shallow angle.

Figure 9:
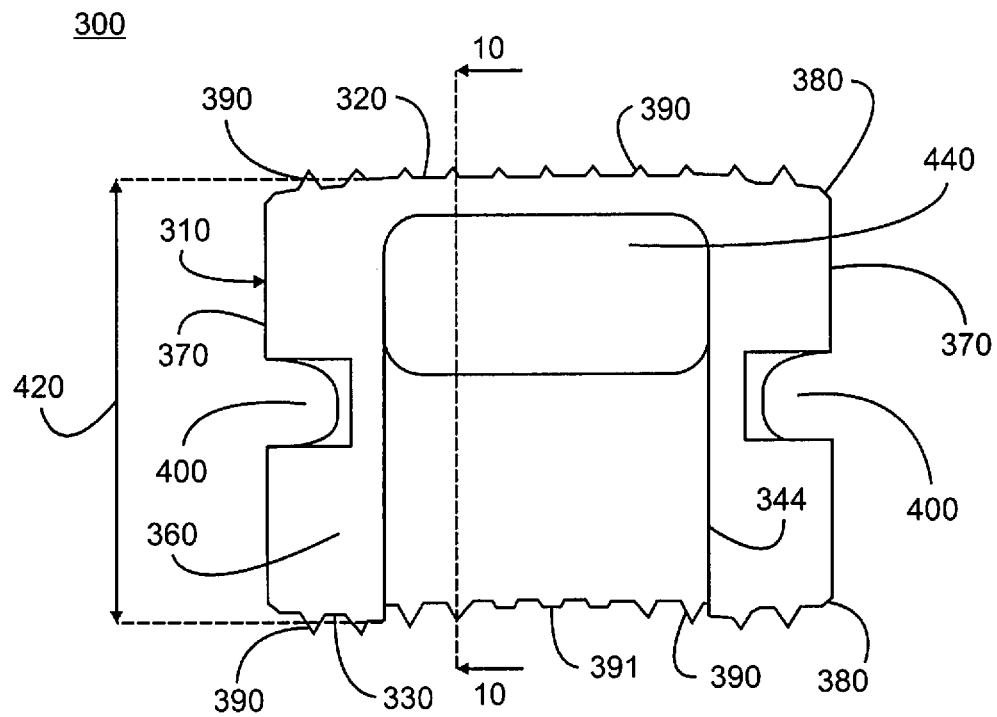
FIG. 9 is a front elevation view of another embodiment of the cervical spine space in accordance with the present invention.
Figure 10:
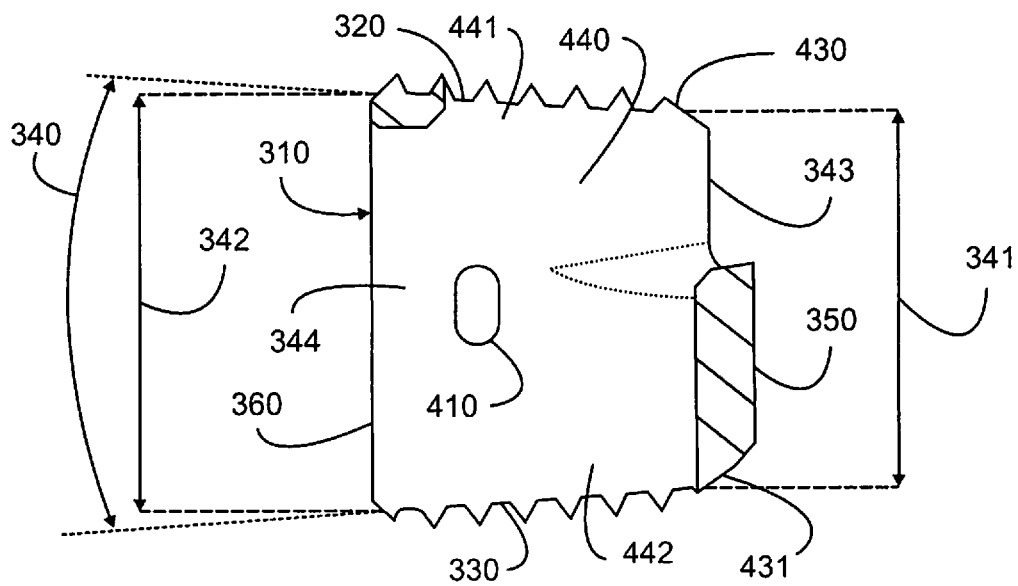
FIG. 10 is a view through line 10-10 of FIG. 9.
Figure 11:
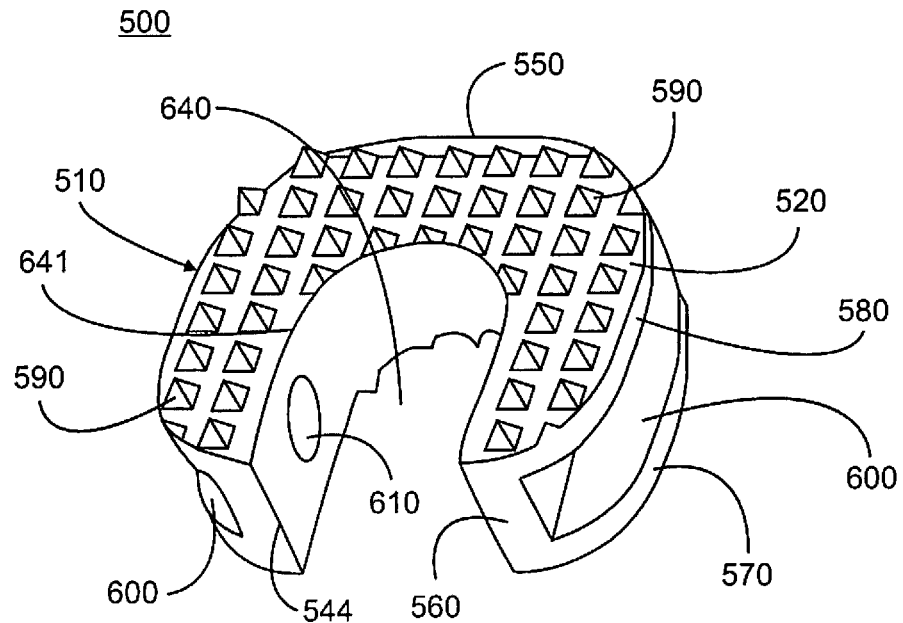
FIG. 11 is a top perspective view of another embodiment of a cervical spine spacer in accordance with the present invention.
Figure 12:
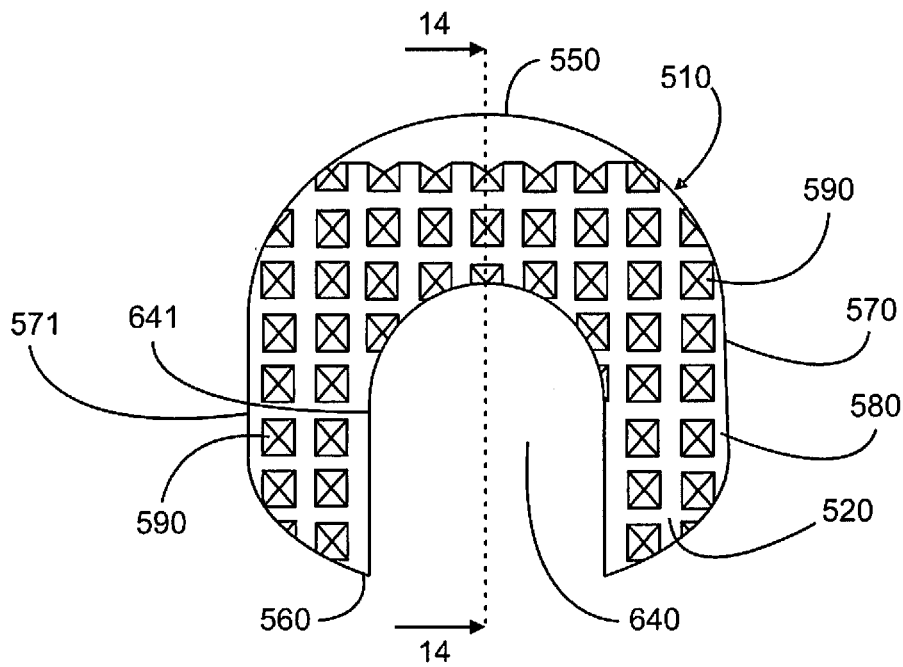
FIG. 12 is a top view of the embodiment of FIG. 11.

As discussed above, the thickness of the spacer body is varied depending on the desired spacing and the location of the spacer along the cervical spine. Referring to FIGS. 9 and 10, another embodiment of a cervical spine spacer 300 in accordance with the present invention is illustrated. The cervical spine spacer 300 includes a spacer body 310 configured to be disposed between and to fit between adjacent cervical vertebrae in the cervical spine. These adjacent cervical vertebrae include a first cervical vertebra that can be the C1, C2, C3, C4, C5 or C6 vertebra and a second cervical vertebra that can be the C2, C3, C4, C5, C6 or C7 vertebra. In one embodiment, the first cervical vertebra is the C1 vertebra, and the second cervical vertebra is the C2 vertebra. The spacer body is sized and shaped to maintain or to re-establish a desired spacing between the adjacent cervical vertebrae. Therefore, the spacer body is constructed from a material that is suitable to be inserted into the cervical spine and that can withstand the movement and forces between adjacent vertebrae in the cervical spine. Suitable materials include, but are not limited to metals such as stainless steel and titanium, plastics and polymers, and elastomers.

The spacer body 310 includes a first surface 320 and a second surface 330 opposite the first surface. When placed between a given pair of adjacent vertebrae in the cervical spine, at least one of the first surface and the second surface is in contact with one of the vertebrae in that given pair of adjacent vertebrae. The first and second surfaces can contact any portion of a given cervical vertebra, including the body, the anterior arch, the posterior arch, the anterior tubercle, the posterior tubercle, the lateral mass and the transverse process. In one embodiment, the adjacent cervical vertebrae are contacted at opposing articular surfaces or articular facets, for example, an inferior articular facet of the first cervical vertebra and an opposing superior articular facet on the second cervical vertebra. In one embodiment, both the first surface and second surface contact one of the vertebra in the given pair of adjacent cervical vertebrae.

The spacer body 310 also includes a front face 350 and a back face 360 opposite the front face. The front and back faces extend between the first and second or top and bottom surfaces of the spacer body. In one embodiment, the back and front faces extend generally perpendicular to the first and second surfaces, although the front and back faces can intersect the first and second surfaces at angles other than 90 degrees. In one embodiment, the front and back faces are configured to be aligned with the anterior and posterior sides of the cervical spine when the cervical spacer is placed between adjacent cervical spine vertebrae. The spacer body also includes a pair of opposing side faces 370 that also extend from the first surface to the second surface. Each side face runs from the front face to the back face. In one embodiment, the side faces extend generally perpendicular to the first and second surfaces, although the side faces can intersect the first and second surfaces at angles other than 90 degrees. In one embodiment, the transitions between the first and second surfaces and the front face, the back face and the side faces include a beveled edge 380. Therefore, the spacer body includes a beveled edge that rounds around the perimeter of the first surface and the second surface. This beveled edge minimizes or eliminates sharp edges that could hinder insertion of the spacer body or that could scrape the vertebrae. In one embodiment, the side faces are configured to be aligned with the lateral sides of the cervical spine when the cervical spacer is placed between adjacent cervical spine vertebrae.

The spacer body is generally rectangular or square in shape; however, the transitions, e.g., the corners of the rectangular shape, between the front and back faces and the side faces are rounded. The transitions between the front face and the side faces and the back face and the side faces are not identical. Therefore, the spacer body is not symmetrical front to back; however, the spacer body is preferably symmetrical side to side. In one embodiment, the rounded transitions from the side faces to the front face have a greater radius or are smoother than the rounded transitions from the side faces to the back face. Therefore, the front face of the spacer body has a more rounded appearance, and the back face has a more squared appearance. In general, the shape of the spacer body, including the transitions among the faces is chosen such that it mirrors or conforms to the shape of the portion of the cervical spine vertebrae that it contacts. For example, the transitions among the faces are configured to fit between opposing articular facets within the space occupied by intervertebral discs. In addition, all of the dimensions of the spacer body are selected to fit within the space between opposing articular facets.

In one embodiment, the spacer body includes a plurality of pointed protrusions 390 located on at least one of the first surface and the second surface. Preferably, the pointed protrusions are located on both the first surface and the second surface. In one embodiment, each pointed protrusion is shaped as a pyramid having a square or rectangular base and extends out from the first or second surface. The pyramid shape can be truncated 391, e.g., frusto-conical, and the pyramid shaped pointed protrusions along the edges of the spacer body can be shaved or clipped by the beveled edge of the spacer body. The pointed protrusions are configured to contact the first cervical vertebra and the second cervical vertebra in the adjacent pair of cervical vertebrae between which the spacer body is positioned. This assists in holding the spacer body in place and prevents undesired movement between the spacer body and the cervical vertebra.

The spacer body includes a groove 400 running along each side face and extending into the spacer body. The groove has a rectangular or rounded cross section and preferably extends along the entire length of each side face. The groove removes mass from the spacer body and also provides a surface for gripping the spacer body using an insertion tool such that the insertion tools does not extend outside the dimensions of the spacer body. At least one hole 410 is provided passing completely through the spacer body. The hole extends through the spacer body perpendicular to the grooves, and the ends of the hole are located in the grooves. The hole also provides a gripping surface for an insertion tool and also provides access to structures such as bone grafts that are surrounded by or contained within the spacer body.

The spacer body is configured to have a desired thickness or height 420 defined between the first surface and the second surface. This thickness is selected based upon the desired spacing to be maintained or established between the adjacent cervical vertebrae. Therefore, the selected thickness can vary depending on the exact vertebra in the adjacent pair of vertebrae and on the location of the cervical spacer between the adjacent pair of vertebrae, e.g., between opposing articular facets or between opposing transverse processes. As illustrated, this thickness 420 is greater than the thickness in the previously described cervical spine spacer 100 embodiment. Therefore, the present embodiment accommodates a large spacing or gap between adjacent cervical vertebrae. In addition, this greater thickness, allows for larger front face and back face portions of the channel openings.

In one embodiment, the thickness is constant between the side faces or the spacer body but varies between the front face 350 and the back face 360. For example, the thickness is smaller at the front face and larger at the back face. In one embodiment, the front face has a first height 341 between the first surface and the second surface, and the back face has a second height 342 between the first surface and the second surface. The first height is less than the second height. The difference in thickness represents an angle 340 between the first surface and the second surface when moving from the front face to the back face. This angle can be varies and matches, for example, changes in distance between opposing portions of the adjacent vertebrae such as opposing articular facets. The spacer body can also include steeper or larger beveled surfaces 430, 431 adjacent the front face between the first surface and the second surface. This larger beveled surface is larger than the beveled perimeter 380 and facilitates insertion of the spacer body between the adjacent cervical vertebrae.

The cervical spine spacer 300 also includes a channel 440 passing completely through the spacer body 310 from the first surface of the spacer body to the second surface of the spacer body. The channel 440 includes a first opening 441 in the first surface and a second opening 442 in the second surface. In one embodiment, the first opening and second opening are completely contained within the first surface and the second surface and do not extend to the edges of the first and second surfaces. Preferably, the first opening extends from the front face, e.g., the edge where the front face meets the first surface, of the spacer body partially across the first surface towards a back face of the spacer body. Similarly, the second opening extends from the back face, e.g., the edge where the back face meets the second surface, partially across the second surface toward the front face. The first opening does not extend completely to the back face, and the second opening does not extend completely to the front face. In addition, both the first and second openings do not extend completely to the side faces.

In one embodiment, the first opening includes a front face portion 343 that extends partially along the front face from the first surface toward the second surface, and the second opening includes a back face portion 344 that extends partially along the back face from the second surface toward the first surface. Although the channel extends along the front face and the back face, the channel is completely enclosed by the spacer body. In this embodiment, the larger thickness of the spacer body yields a larger channel that can accommodate larger bone grafts spanning greater distances between adjacent cervical vertebrae.

Referring now to FIGS. 11-16, another exemplary embodiment of a cervical spine spacer 500 in accordance with the present invention is illustrated. This embodiment illustrates a cervical spine spacer that is U-shaped with an open channel to accommodate insertion around a bone graft or other structure and a greater range of angles between a fastener passing through the channel and the spacer body. The cervical spine spacer includes a spacer body 510. The spacer body is configured to be disposed between and to fit between adjacent cervical vertebrae in the cervical spine. These adjacent cervical vertebrae include a first cervical vertebra that can be the C1, C2, C3, C4, C5 or C6 vertebra and a second cervical vertebra that can be the C2, C3, C4, C5, C6 or C7 vertebra. In one embodiment, the first cervical vertebra is the C1 vertebra, and the second cervical vertebra is the C2 vertebra. The spacer body is sized and shaped to maintain or to re-establish a desired spacing between the adjacent cervical vertebrae. Therefore, the spacer body is constructed from a material that is suitable to be inserted into the cervical spine and that can withstand the movement and forces between adjacent vertebrae in the cervical spine. Suitable materials include, but are not limited to metals such as titanium and plastics, polymers and elastomers.

The spacer body 510 includes a first surface 520 and a second surface 530 opposite the first surface. When placed between a given pair of adjacent vertebrae in the cervical spine, at least one of the first surface and the second surface is in contact with one of the vertebra in that given pair of adjacent vertebrae. The first and second surfaces can contact any portion of a given cervical vertebra, including the body, the anterior arch, the posterior arch, the anterior tubercle, the posterior tubercle, the lateral mass and the transverse process. In one embodiment, the adjacent cervical vertebrae are contacted at opposing articular surfaces or articular facets, for example, an inferior articular facet of the first cervical vertebra and an opposing superior articular facet on the second cervical vertebra. In one embodiment, both the first surface and second surface contact one of the vertebrae in the given pair of adjacent cervical vertebrae.

The spacer body 510 also includes a front face 550 and a back face 560 opposite the front face. The front and back faces extend between the first and second or top and bottom surfaces of the spacer body. In one embodiment, the back and front faces extend generally perpendicular to the first and second surfaces, although the front and back faces can intersect the first and second surfaces at angles other than 90 degrees. In one embodiment, the front and back faces are configured to be aligned with the anterior and posterior sides of the cervical spine when the cervical spacer is placed between adjacent cervical spine vertebrae. The spacer body also includes a pair of opposing side faces 570 that also extend from the first surface to the second surface. Each side face runs from the front face to the back face. In one embodiment, the side faces extend generally perpendicular to the first and second surfaces, although the side faces can intersect the first and second surfaces at angles other than 90 degrees. In one embodiment, the transitions between the first and second surfaces and the front face, the back face and the side faces include a beveled edge 580. Therefore, the spacer body includes a beveled edge that rounds around the perimeter of the first surface and the second surface. This beveled edge minimizes or eliminates sharp edges that could hinder insertion of the spacer body or that could scrape the vertebrae. In one embodiment, the side faces are configured to be aligned with the lateral sides of the cervical spine when the cervical spacer is placed between adjacent cervical spine vertebrae.

The spacer body is generally rectangular or square in shape; however, the transitions, e.g., the corners of the rectangular shape, between the front and back faces and the side faces are rounded. The transitions between the front face and the side faces and the back face and the side faces are not identical. Therefore, the spacer body is not symmetrical front to back; however, the spacer body is preferably symmetrical side to side. In one embodiment, the rounded transitions from the side faces to the front face have a greater radius or are smoother than the rounded transitions from the side faces to the back face. Therefore, the front face of the spacer body has a more rounded appearance, and the back face has a more squared appearance. In general, the shape of the spacer body, including the transitions among the faces is chosen such that it mirrors or conforms to the shape of the portion of the cervical spine vertebra that it contacts. For example, the transitions among the faces are configured to fit between opposing articular facets within the space occupied by intervertebral discs. In addition, all of the dimensions of the spacer body are selected to fit within the space between opposing articular facets.

In one embodiment, the spacer body includes a plurality of pointed protrusions 590 located on at least one of the first surface and the second surface. Preferably, the pointed protrusions are located on both the first surface and the second surface. In one embodiment, each pointed protrusion is shaped as a pyramid having a square or rectangular base and extends out from the first or second surface. The pyramid shape can be truncated, e.g., frusto-conical, and the pyramid shaped pointed protrusions along the edges of the spacer body can be shaved or clipped by the beveled edge of the spacer body. The pointed protrusions are configured to contact the first cervical vertebra and the second cervical vertebra in the adjacent pair of cervical vertebrae between which the spacer body is positioned. This assists in holding the spacer body in place and prevents undesired movement between the spacer body and the cervical vertebrae.

The spacer body includes a groove 600 running along each side face and extending into the spacer body. The groove has a rectangular or rounded cross section and preferably extends along the entire length of each side face. The groove removes mass from the spacer body and also provides a surface for gripping the spacer body using an insertion tool such that the insertion tools does not extend outside the dimensions of the spacer body. At least one and preferably two or more holes 610 are provided passing completely through the spacer body. These holes extend through the spacer body perpendicular to the grooves, and the ends of the holes are located in the grooves. These holes also provide a gripping surface for an insertion tool and also provide access to structures such as bone grafts that are surrounded by or contained within the spacer body. As illustrated, some holes pass completely through the spacer body, or at least completely into the channel, and other holes only extend partially into the spacer body.

Figures 13, 14:
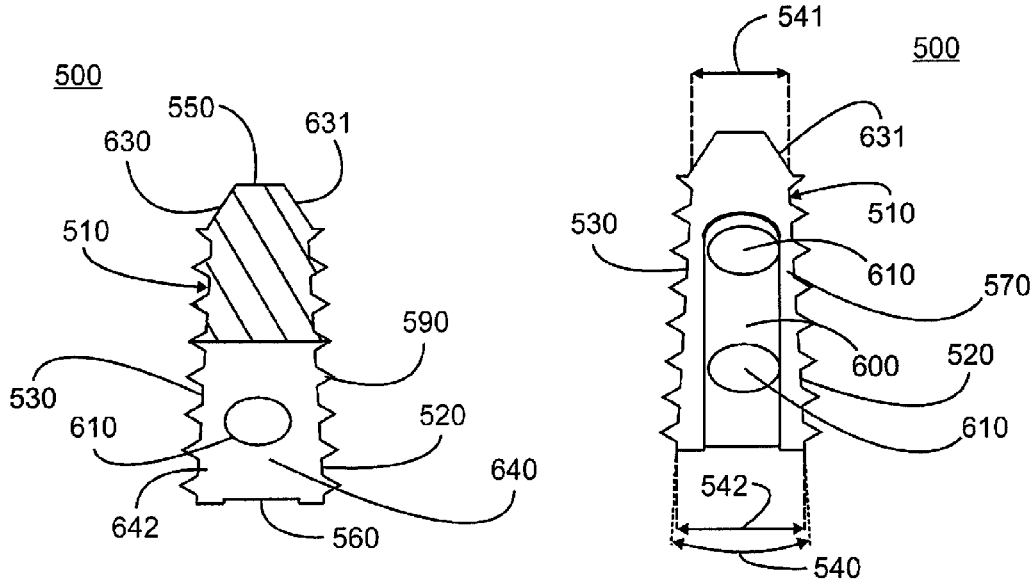
FIG. 13 is a side elevation view of the embodiment of FIG. 11.
FIG. 14 is a view through line 14-14 of FIG. 12.
Figure 15:
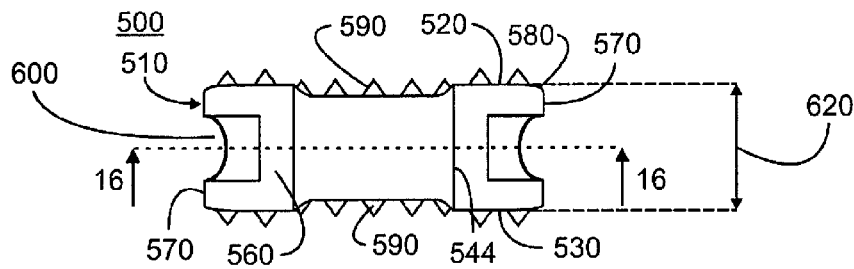
FIG. 15 is a back elevation view of the embodiment of FIG. 11.
Figure 16:
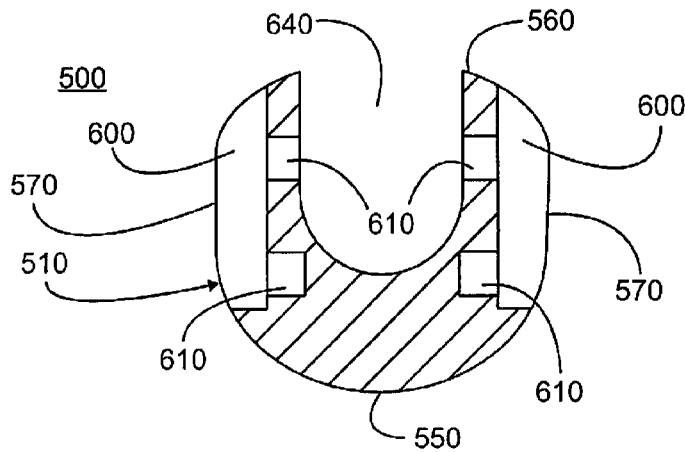
FIG. 16 is a view through line 16-16 of FIG. 15.

The spacer body is configured to have a desired thickness or height 620 (FIG. 15) defined between the first surface and the second surface. This thickness is selected based upon the desired spacing to be maintained or established between the adjacent cervical vertebrae. Therefore, the selected thickness can vary depending on the exact vertebra in the adjacent pair of vertebrae and on the location of the cervical spacer between the adjacent pair of vertebrae, e.g., between opposing articular facets or between opposing transverse processes. In one embodiment, the thickness is constant between the side faces or the spacer body but varies between the front face 550 and the back face 560 (FIG. 13). For example, the thickness is smaller at the front face and larger at the back face. In one embodiment, the front face has a first height 541 between the first surface and the second surface, and the back face has a second height 542 between the first surface and the second surface. The first height is less than the second height. The difference in thickness represents an angle 540 between the first surface and the second surface when moving from the front face to the back face. This angle can be varied and matches, for example, changes in distance between opposing portions of the adjacent vertebrae such as opposing articular facets. In one embodiment, this angle is between about 5° and about 10°, preferably about 7°. The spacer body can also include steeper or larger beveled surfaces 630, 631 adjacent the front face between the first surface and the second surface. This larger beveled surface is larger than the beveled perimeter 580 and facilitates insertion of the spacer body between the adjacent cervical vertebrae.

The cervical spine spacer 500 also includes a channel 640 passing completely through the spacer body 510 from the first surface of the spacer body to the second surface of the spacer body. The channel 640 includes a first opening 641 in the first surface and a second opening 642 in the second surface. The first opening extends from the back face, e.g., the edge where the back face meets the first surface, of the spacer body partially across the first surface towards a front face of the spacer body. Similarly, the second opening extends from the back face, e.g., the edge where the back face meets the second surface, partially across the second surface toward the front face. Both the first and second openings for not extend completely to the side faces. Alternatively, both the first and second openings can extend from the front face toward the back face.

The channel also includes a back face portion 544 that extends completely along the back face from the second surface to the first surface and is in communication with both the first opening and the second opening. Therefore, the channel is not completely enclosed by the spacer body. This yields a spacer body having a distinctive U-shape within an open channel. The open channel facilitates insertion of the cervical spine spacer around structures in the cervical spine. In addition, an even shallower angle is facilitated between the fastener and the first or second surfaces of the spacer body.

Figure 17:
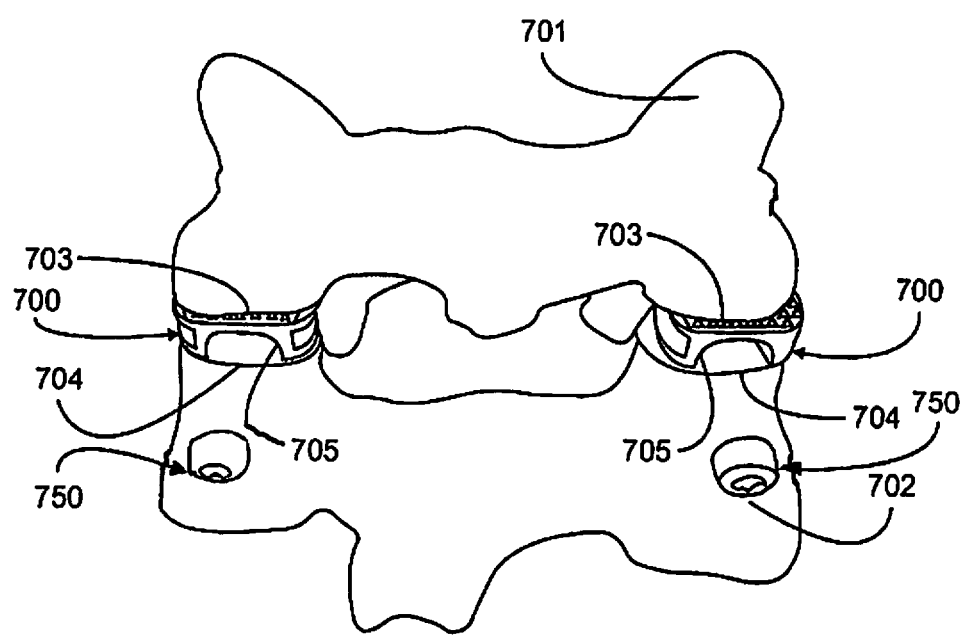
FIG. 17 is a representation of an embodiment of a pair of cervical spine spacers between two cervical vertebrae in accordance with the present invention.

In one embodiment, the spacer body of all embodiments of the cervical spine spacer in accordance with the present invention is sized and shaped to fit within the space between the opposing articular facets, for example in the space typically occupied by an intervertebral disc. Referring to FIG. 17, a pair of cervical spine spacers 700 is inserted between a first cervical vertebra 701 and a second cervical vertebra 702. In some embodiments, the first cervical vertebra can be the C1 through C6 vertebrae, and the second cervical vertebra can be the C2 through C7 vertebrae. Each spacer is placed between the superior articular facet 703 of the first cervical vertebra and the inferior articular facet 705 of the second cervical vertebra. A fastener 750, e.g., a screw, can be passed in a direction from the second cervical vertebra 702, through the spacer 700 and into the second cervical vertebra 701, e.g., from an inferior position to a superior position. In other embodiments, the screw can be passed in a direction from the first cervical vertebra to the second cervical vertebra. The shape of the channel accommodates the direction of insertion of the fastener, and access to the interior of the channel is provided, for example, by the back face portion 705 of the channel opening, which is exposed in a posterior position based on the direction of insertion of the spacer.

Figure 18:
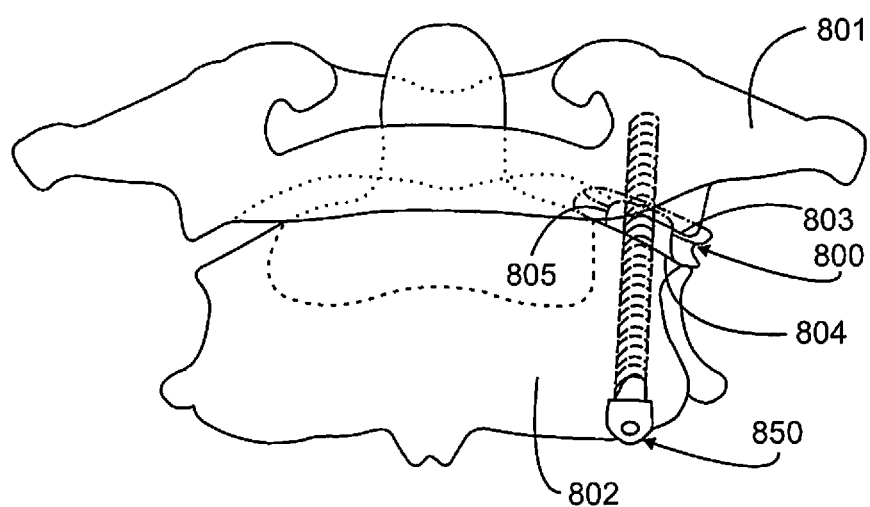
FIG. 18 is a representation of an embodiment of a cervical spine spacer between the atlas and the axis in accordance with the present invention.
Figure 19:
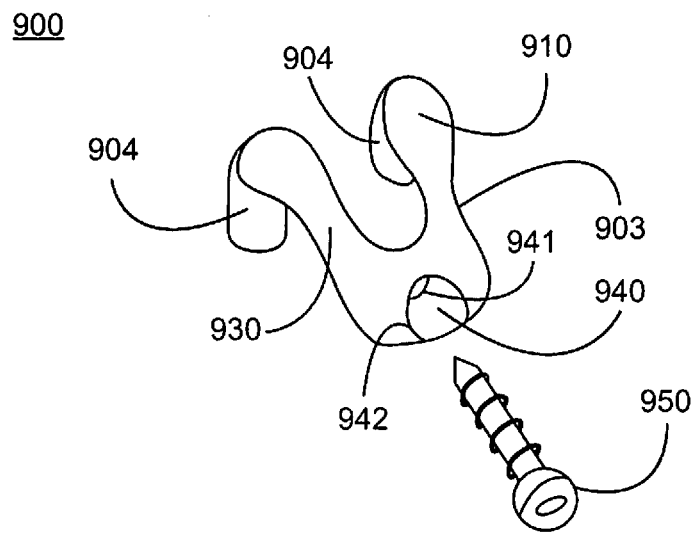
FIG. 19 is a representation illustrating a perspective view of another embodiment of the cervical spine spacer in accordance with the present invention.
Figure 20:
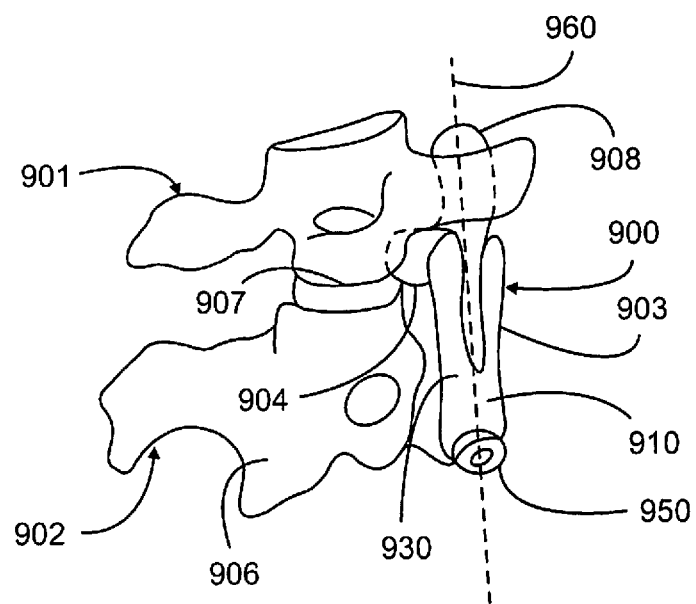
FIG. 20 is a representation illustrating a lateral view of the cervical spine spacer embodiment of FIG. 19 disposed between the atlas and the axis.
Figure 21:
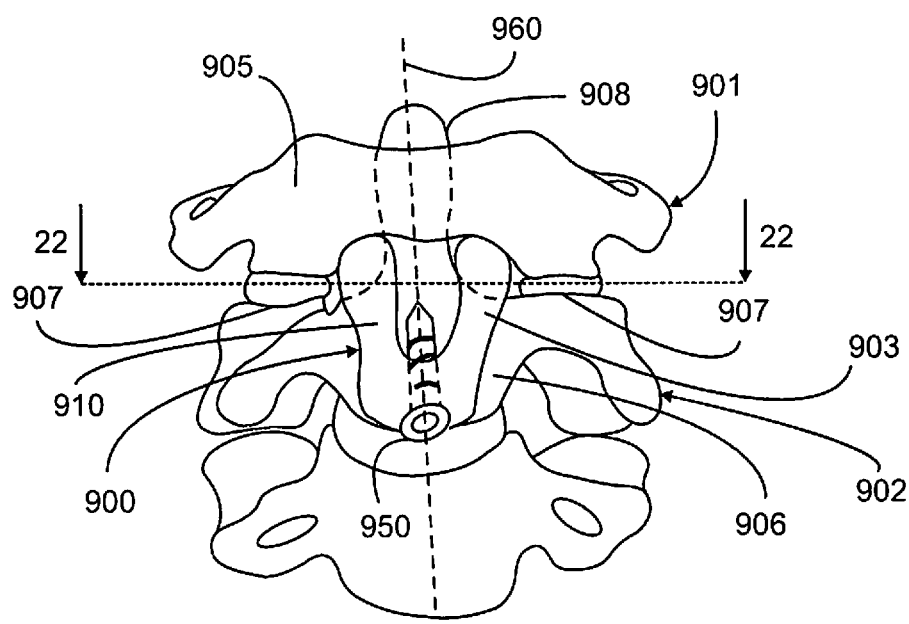
FIG. 21 is a representation illustrating an anterior view of the cervical spine spacer embodiment of FIG. 19 disposed between the atlas and the axis.
Figure 22:
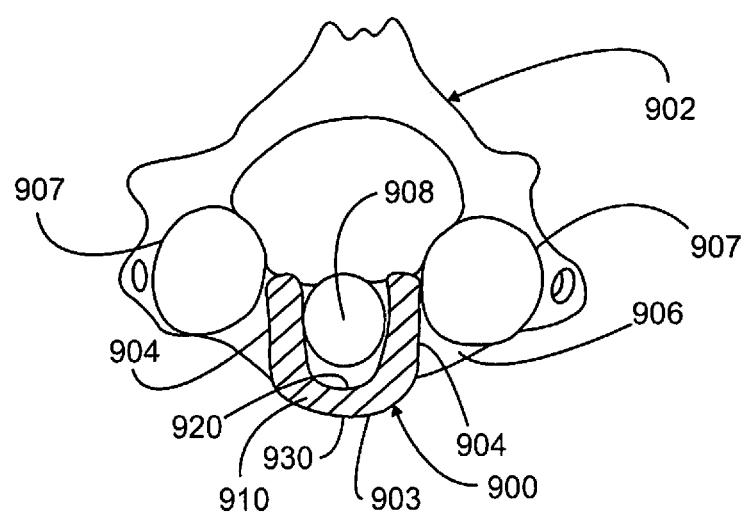
FIG. 22 is a view through line 22-22 of FIG. 21.

Referring to FIG. 18, a cervical spine spacer 800 is inserted between a first cervical vertebra 801 and a second cervical vertebra 802. The first cervical vertebra is the C1 vertebra or atlas, and the second cervical vertebra is the C2 vertebra or axis. The spacer is placed between the superior articular facet 803 of the first cervical vertebra and the inferior articular facet 805 of the second cervical vertebra. A fastener 850, e.g., a screw, a passed in a direction from the second cervical vertebra 802, through the spacer 800 and into the first cervical vertebra 801, e.g., from an inferior position to a superior position, as the skull inhibits access in the other direction. The shape of the channel accommodates this routing of the fastener, and access to the interior of the channel is provided, for example, by the back face portion 805 of the channel opening, which is exposed in a posterior position based on the direction of insertion of the spacer. Suitable methods and tools for access the cervical spine, inserting spacers and inserting and securing fasteners are known and available in the art.

Referring to FIGS. 19-22, another exemplary embodiment of a cervical spine spacer 900 in accordance with the present invention is illustrated. The cervical spine spacer includes a spacer body 910. The spacer body is configured to be disposed between and to fit between adjacent cervical vertebrae in the cervical spine. These adjacent cervical vertebrae include a first cervical vertebra that can be the C1, C2, C3, C4, C5 or C6 vertebra and a second cervical vertebra that can be the C2, C3, C4, C5, C6 or C7 vertebra. In one embodiment as illustrated, the first cervical vertebra 901 is the C1 vertebra or atlas, and the second cervical vertebra 902 is the C2 vertebra or axis. The spacer body is sized and shaped to maintain or to re-establish a desired spacing between the adjacent cervical vertebrae. Therefore, the spacer body is constructed from a material that is suitable to be inserted into the cervical spine and that can withstand the movement and forces between adjacent vertebrae in the cervical spine. Suitable materials include, but are not limited to metals such as titanium and plastics, polymers and elastomers.

The spacer body 910 includes a first surface 920 and a second surface 930 opposite the first surface. When placed between a given pair of adjacent vertebrae in the cervical spine, the first surface is in contact with one of the vertebrae in that given pair of adjacent vertebrae. In particular, the first surface is in contact with the anterior side of the second cervical vertebrae. The spacer body includes at least one spacer portion 904 configured to be disposed between the adjacent cervical vertebrae and an anchor plate portion 903 extending from the spacer portion. In one embodiment, the anchor plate portion extends from the spacer portion at an angle of about 90°. The first surface along the anchor plate portion is in contact with the anterior surface of the second or C2 vertebra. The first surface along the spacer portion is in contact with another portion of the second vertebra, and the second surface is on contact with the first vertebra. In one embodiment, the spacer body includes two separate and independent spacer portions. The separate and independent spacer portions are disposed between different portions of the first and second cervical vertebra. The anchor plate portion is U-shaped having two arms, and each spacer portion extends from a given arm of the U-shaped anchor plate portion at the 90° angle.

Each cervical spine spacer 900 spacer portion 904 is configured to be disposed between an anterior arch 905 of the C1 vertebra and the body 906 of the C2 vertebra between one of a pair of superior articular facets 907 and the odontoid process 908. When the spacer body includes two spacer portions, each spacer portion extends from the anchor plate and is disposed between the anterior arch of the C1 vertebra and the body of the C2 vertebra such that each spacer body is on an opposite side of the odontoid process.

The cervical spine spacer 900 also includes a fastener 950 a channel 940 passing completely through the spacer body 910 from the first surface of the spacer body to the second surface of the spacer body. The channel 940 includes a first opening 941 in the first surface and a second opening 942 in the second surface. The channel is sized and shaped to accommodate the fastener, which is typically a screw that is passed through the channel from the second opening to the first opening and into the second cervical vertebra. In one embodiment, the fastener extends into the second cervical vertebra along an axis running through the odontoid process along a trajectory that is the same as those of odontoid screws used to repair a fractured odontoid process. In one embodiment, the fastener is removed and replaced with a longer odontoid screw. In one embodiment, the channel passes through the anchor plate portion intersecting the first surface and the second surface at an angle configured to direct a fastener through the anterior surface of the C2 vertebra from an inferior position toward the odontoid process of the C2 vertebra.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s) and steps or elements from methods in accordance with the present invention can be executed or performed in any suitable order. Therefore, it will be understood that the appended claims are intended to cover all such modifications and embodiments, which would come within the spirit and scope of the present invention.

What is claimed is:

1. A cervical spine spacer comprising:
a u-shaped spacer body having a front face, a back face, an upper surface, a lower surface, a first side surface and a second side surface, the spacer body configured to be disposed between adjacent cervical vertebrae in the cervical spine and to maintain a desired spacing between the adjacent cervical vertebrae; and
an open channel, defined by a u-shaped wall comprising sidewalls that are substantially parallel to the first side surface and the second side surface, the open channel passing completely through the spacer body from the upper surface of the spacer body to the lower surface of the spacer body and extending from the back face partially across the upper and lower surfaces towards the front face, at least one of the upper surface and the lower surface configured to contact one of the adjacent cervical vertebrae,
wherein the spacer body comprises a first groove on the first side surface of the spacer body and a second groove configured on the second side surface of the spacer body,
wherein the spacer body includes a first hole positioned within the first groove and extending through the first side surface of the spacer body perpendicular to the first groove and extending towards the second side surface and a second hole positioned within the second groove and extending through the second side surface of the spacer body perpendicular to the second groove and extending towards the first side surface,
wherein the first and second holes are blind holes that extend only partially into the spacer body, wherein the first hole and second hole are configured to receive an insertion tool, wherein the spacer is devoid of any apertures for receiving fasteners to secure the spacer to adjacent cervical vertebrae.

2. The cervical spine spacer of claim 1, further comprising a fastener extending through at least a portion of the open channel and configured to anchor the spacer body between the adjacent cervical vertebrae.

3. The cervical spine spacer of claim 2, wherein the fastener has an overall length sufficient to pass through a first vertebra, through the channel in the spacer body, and through a second vertebra.

4. The cervical spine spacer of claim 1, wherein the channel is configured to accommodate a fastener extending through the channel and intersecting each one of the upper surface and the lower surface at a plurality of different angles.

5. The cervical spine spacer of claim 1, wherein the upper surface is configured to contact a first cervical vertebra and the lower surface is configured to contact a second cervical vertebra.

6. The cervical spine spacer of claim 5, wherein the first cervical vertebra comprises a C1, C2, C3, C4, C5 or C6 vertebra and the second cervical vertebra comprises a C2, C3, C4, C5, C6 or C7 vertebra.

7. The cervical spine spacer of claim 5, wherein the upper surface is configured to contact an inferior articular facet of the first cervical vertebra and the lower surface is configured to contact a superior articular facet of the second cervical vertebra.

8. The cervical spine spacer of claim 7, wherein the first cervical vertebra comprises a C1 vertebra and the second cervical vertebra comprises a C2 vertebra.

9. The cervical spine spacer of claim 5, wherein the upper surface comprises a plurality of pointed protrusions extending out from the upper surface and configured to contact the first cervical vertebra and the lower surface comprise a plurality of pointed protrusions extending out from the lower surface and configured to contact the second cervical vertebra.

10. The cervical spine spacer of claim 1, wherein:
the front face comprises a first height between the upper surface and the lower surface; and
the back face comprises a second height between the upper surface and the lower surface, the first height less than the second height.

11. The cervical spine spacer of claim 1, wherein the spacer body includes a beveled edge that rounds a perimeter of at least one of the upper and lower surfaces.

12. A cervical spine device comprising:
a u-shaped spacer body configured to be disposed between adjacent cervical vertebrae in the cervical spine and to maintain a desired spacing between the adjacent cervical vertebrae;
an open channel, defined by a u-shaped wall comprising sidewalls that are substantially parallel to the first side surface and the second side surface, the open channel passing completely through the spacer body from an upper surface of the spacer body to a lower surface of the spacer body and extending from a back face partially across the first and second surfaces towards a front face; and
a fastener extending through the channel and configured to anchor the spacer body between the adjacent cervical vertebrae;

wherein the first surface is configured to contact an inferior articular facet of a first cervical vertebra in the adjacent cervical vertebrae, the second surface is configured to contact a superior articular facet of a second cervical vertebra in the adjacent cervical vertebrae, and the channel is configured to accommodate at least a portion of the fastener extending through the channel and intersecting each one of the first surface, the second surface, the inferior articular facet and the superior articular facet at a plurality of different angles, wherein the channel is shaped to accommodate insertion of the fastener in a first direction of insertion through the channel and into the first cervical vertebra and insertion of the fastener in a second direction of insertion through the channel and into the second cervical vertebra from a plurality of directions, wherein the device is devoid of any apertures for receiving fasteners to secure the device to adjacent cervical vertebrae.

13. The cervical spine device of claim 12, wherein the spacer body comprises a first groove and a second groove configured on a first side surface and a second side surface of the spacer body.

14. The cervical spine device of claim 13, wherein the first and second grooves extend along an entire length of each of the first and second side surfaces.

15. The cervical spine device of claim 13, wherein the spacer body includes at least one hole positioned within at least one of the first groove and the second groove and extending through the first or second side surface of the spacer body perpendicular to the first or second groove.

16. The cervical spine device of claim 15, wherein the at least one hole is in fluid communication with the open channel.

17. A cervical spine device comprising:
a u-shaped spacer body having a front face, a back face, an upper surface, a lower surface, a first side surface and a second side surface, the spacer body configured to be disposed between adjacent cervical vertebrae in the cervical spine and to maintain a desired spacing between the adjacent cervical vertebrae; the spacer body defining an open channel having a u-shaped wall comprising sidewalls that are substantially parallel to the first side surface and the second side surface, the open channel passing completely through the spacer body from the upper surface to the lower surface of the spacer body and extending from the back face partially across the upper and lower surfaces towards the front face, at least one of the upper surface and the lower surface configured to contact one of the adjacent cervical vertebrae, and a fastener extending through at least a portion of the open channel and configured to anchor the spacer body between the adjacent cervical vertebrae, wherein the channel is shaped to accommodate insertion of the fastener in a first direction of insertion through the channel and into a first cervical vertebra and insertion of the fastener in a second direction of insertion through the channel and into a second cervical vertebra from a plurality of directions, wherein the device is devoid of any apertures for receiving fasteners to secure the device to adjacent cervical vertebrae.

18. The cervical spine device of claim 17, wherein the spacer body comprises a first groove and a second groove configured on each one of the first side surface and the second side surface of the spacer body, and wherein the spacer body includes a first hole positioned within the first groove and extending through the first side surface of the spacer body perpendicular to the first groove and extending towards the second side surface and a second hole positioned within the second groove and extending through the second side surface of the spacer body perpendicular to the second groove and extending towards the first side surface.

19. The cervical spine spacer of claim 1, wherein the spacer body includes a third hole positioned within the first groove and extending through the first side surface of the spacer body perpendicular to the first groove and extending towards the second side surface and a fourth hole positioned within the second groove and extending through the second side surface of the spacer body perpendicular to the second groove and extending towards the first side surface, wherein the third and fourth holes are in fluid communication with the open channel.

* * * * *